United States Patent [19]

Gordon

[11] Patent Number: Plant 7,081

[45] Date of Patent: Dec. 19, 1989

[54] WORLD FEEDER BERMUDA GRASS

[76] Inventor: Louis R. Gordon, P.O. Box 516, Bethany, Okla. 73008

[21] Appl. No.: 280,227

[22] Filed: Dec. 5, 1988

[51] Int. Cl.[4] ..... A01H 5/00

[52] U.S. Cl. ..... Plt./88

[58] Field of Search ..... Plt./88

*Primary Examiner*—Robert E. Bagwill

[57] ABSTRACT

A variety of Bermuda grass, called World Feeder, having all the desirable traits of Alicia Bermuda grass plus excellent cold hardiness.

1 Drawing Sheet

1

World Feeder Bermuda grass is a mutant developed through selection on my acreage in Bethany, Okla. It comes from a planting in 1973 of Alicia Bermuda grass and has all of the good qualities of Alicia. However, the drawback of Alicia was that it was not winter hardy in colder climates. The major difference is that World Feeder Bermuda grass has proven winter hardy. It has thrived in the face of severe winters, where there were days on end of −5 to +10 degrees Fahrenheit with wind chill factors of −20 to −30 degrees. No winter kill has been evidenced during this time.

The World Feeder Bermuda grass is a fast growing, hybrid Bermuda grass, averaging knee high in summer, growing approximately 1 inch per day in warm weather, has a deep penetrating root system, and is tender and succulent for pasture grazing and hay. The crude protein averages around 19% plus, with digestible protein approximately 75%. Tests show the crude fiber to be 16% and the fat 2.5%. It has great drought resistant qualities due to the deep root system and has a sweet taste. It retains 50% of its greenness even after a killing frost (November 1st in Oklahoma) and stays

2 relatively green until late December. Emergence begins in April and by June 1 is in full growth.

'World Feeder' Bermuda grass, *Cynodon dactylon* var. aridus (seems to be the same variety as Alicia) is a stoloniferous sward-forming perennial with sparse long, slender, deeply penetrating rhizomes; surface stolons slender and very fast spreading, sometimes reaching lengths of 10–12 meters; culms slender, 8–40 cm. high and 0.5–1.25 mm. in diameter. Leaf-blades flat, or folded when dry, often short and narrow, 1–12 cm. long and 2–4 mm. wide, glaucous, scaberulous, with or without scattered hairs; liqule a membranous rim 0.2–0.3 mm. long, ciliate on the edge. Inflorescences few with 4–6 racemes usually 4–6 cm. long, in a single whorl. Spikelets 2–2.5 mm. long; glumes lanceolate in side view, 1-nerved, the upper $\frac{1}{2}$–$\frac{3}{4}$ as long as the spikelet; lemma silky pubescent on the keel; palea glabrous. Growth habit results in production of a very loose mat rather than a turf.

I claim:

1. A new variety of Bermuda grass as shown and described.

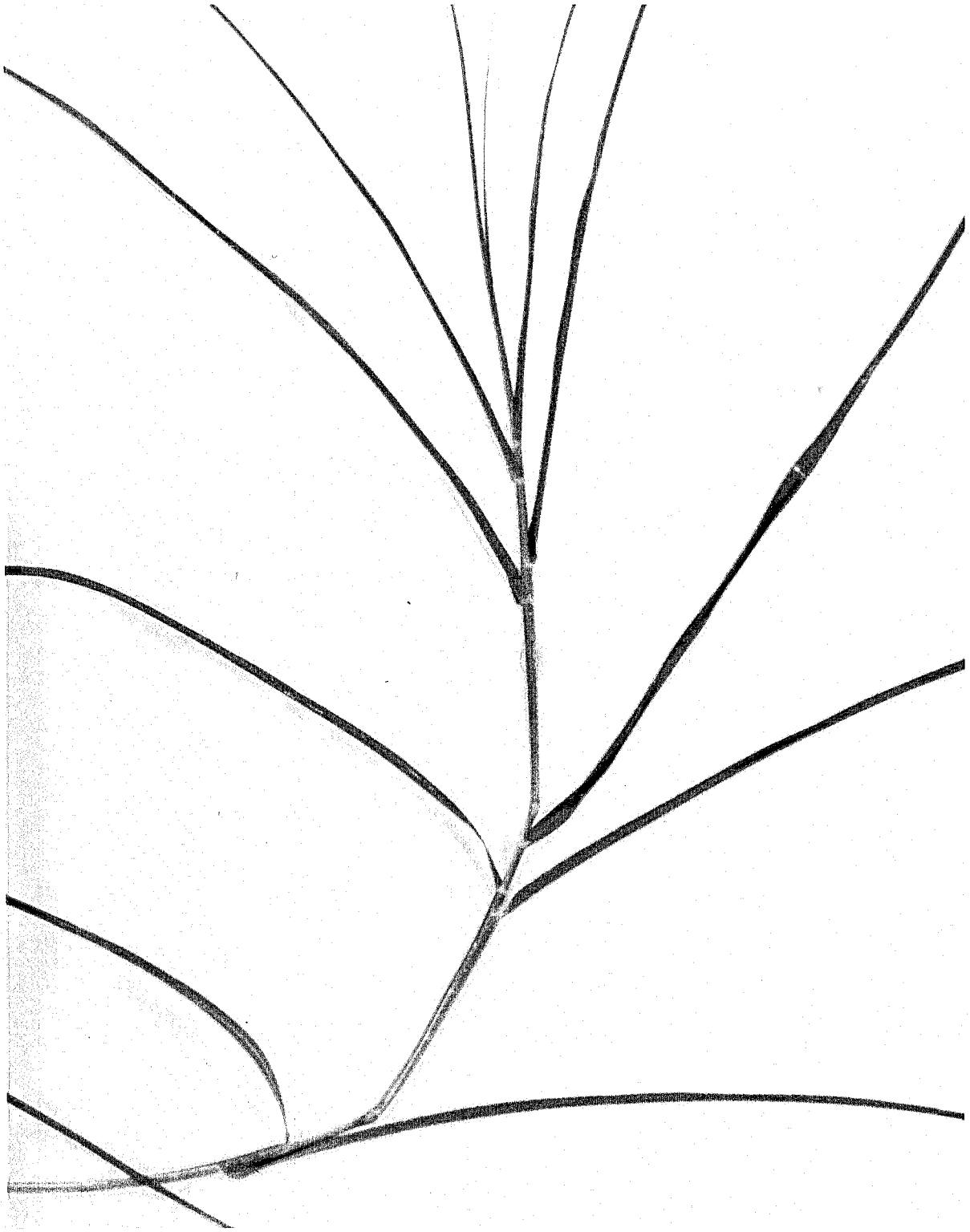

* * * * *